US008097607B2

(12) United States Patent
Cabana et al.

(10) Patent No.: US 8,097,607 B2
(45) Date of Patent: *Jan. 17, 2012

(54) LOW DOSE RIFALAZIL COMPOSITIONS

(76) Inventors: Bernard E. Cabana, Montgomery Village, MD (US); Arthur F. Michaelis, Devon, PA (US); Gary P. Magnant, Topsfield, MA (US); Chalom B. Sayada, Luxembourg (LU)

(*) Notice: Subject to any disclaimer, the term of this patent is extended or adjusted under 35 U.S.C. 154(b) by 447 days.

This patent is subject to a terminal disclaimer.

(21) Appl. No.: 10/668,792

(22) Filed: Sep. 23, 2003

(65) Prior Publication Data

US 2004/0157840 A1 Aug. 12, 2004

Related U.S. Application Data

(60) Provisional application No. 60/412,958, filed on Sep. 23, 2002.

(51) Int. Cl.
*A61K 31/33* (2006.01)
(52) U.S. Cl. ........................................... 514/183
(58) Field of Classification Search .................. None
See application file for complete search history.

(56) References Cited

U.S. PATENT DOCUMENTS

| | | | | |
|---|---|---|---|---|
| 4,983,602 | A | 1/1991 | Yamane et al. | 514/229.5 |
| 5,547,683 | A | 8/1996 | Yano et al. | 424/501 |
| 5,786,349 | A | 7/1998 | Yamashita et al. | 514/183 |
| 5,981,522 | A | 11/1999 | Yamashita et al. | 514/224.5 |
| 6,316,433 | B1 | 11/2001 | Rose et al. | 514/183 |
| 6,486,161 | B1 | 11/2002 | Fujii et al. | 514/252.13 |
| 6,566,354 | B1 | 5/2003 | Montgomery et al. | 514/183 |
| 2003/0203903 | A1 | 10/2003 | Rose et al. | 514/229.8 |
| 2003/0236265 | A1* | 12/2003 | Sayada | 514/252.13 |
| 2004/0014750 | A1* | 1/2004 | Michaelis et al. | 514/224.5 |
| 2004/0034021 | A1 | 2/2004 | Michaelis et al. | 514/310 |
| 2004/0077533 | A1 | 4/2004 | Sayada | 514/8 |
| 2004/0106590 | A1* | 6/2004 | Eisenstein | 514/183 |
| 2004/0126414 | A1 | 7/2004 | Michaelis | 514/224.5 |
| 2004/0176404 | A1 | 9/2004 | Sayada | 514/252.13 |
| 2005/0137189 | A1* | 6/2005 | van Duzer et al. | 514/224.5 |
| 2005/0143409 | A1* | 6/2005 | Michaelis et al. | 514/291 |

OTHER PUBLICATIONS

Lithander et al., British Journal of Ophthalmology, 2001, 85:371.*
Remington's Pharmaceutical Sciences, (1975) 15th edition, p. 703.*
"Rifalazil PathoGenesis Plans Phase II Studies," R&D Focus Drug News. Jun. 9, 1997.
Bermudez et al., "Activity of KRM 1648 Alone or in Combination with Ethambutol or Clarithromycin Against *Mycobacterium avium* in Beige Mouse Model of Disseminated Infection," *Antimicrobial Agents and Chemotherapy* 38(8):1844 (1994).
Dietze et al., "Safety and Bactericidal Activity of Rifalazil in Patients with Pulmonary Tuberculosis," *Antimicrobial Agents and Chemotherapy* 45(7):1972 (2001).
Dhople AM, "In Vivo Susceptibility of *Mycobacterium ulcerans* to KRM-1648, A New Benzoxazinorifamycin, in Comparison with Rifampicin," *Arzneimiffelforschung* 51(6):501 (2001).

Emori et al., "Evaluation of in Vivo Therapeutic Efficacy of a New Benzoxazinorifamycin, KRM-1648, in SCID Mouse Model for Disseminated *Mycobacterium avium* Complex Infection," *International Journal of Antimicrobial Agents* 10(1):59 (1998).
Fujii et al., "In Vitro and In Vivo Antibacterial Activities of KRM-1648 and KRM-1657, New Rifamycin Derivatives," *Antimicrobial Agents and Chemotherapy* 38:1118, (1994).
Gidoh et al., "Bactericidal Action at Low Doses of a New Rifamycin Derivative, 3'-hydroxy-5'-(4-isobutyl-1-piperazinyl) Benzoxazinorifamycin (KRM-1648) on *Mycobacterium leprae* Inoculated into Ffootpads of Nude Mice," *Leprosy Review* 63(4):319 (1992).
Heep et al, "Detection of Rifabutin Resistance and Association of rpoB Mutation S with Resistance to Four Rifamycin Derivatives in *Helicobacter pylori*," *Journal of Clinical Microbiology & Infectious Diseases* 21:143 (2002).
Hirara et al., "In Vitro and in Vivo Activities of the Benezoxazinorifamycin KRM-1648 Against *Mycobacterium tuberculosis*," *Antimocrobial Agents and Chemotherapy* 39 (10):2295 (1995).
Hosoe et al., "Identification and Antimicrobial Activity of Urinary Metabolites of a Rifamycin Derivative in Dog," *Xenoblotica* 26(3):321 (1996).
Hosoe et al., "Pharmacokinetics of KRM-1648, a New Benzoxazinorifamycin, in Rats and Dogs," *Antimicrobial and Chemotherapy* 40(12):2749 (1996).
Ji et al., "How Effective is KRM-1648 in Treatment of Disseminated *Mycobacterium avium* Complex Infections in Beige Mice?," *Antimicrobial Agents and Chemotherapy* 40(2):437 (1996).
Kelly et al., "Low-Dose Aerosol Infection Model for Testing Drugs for Efficacy Against *Mycobacterium tuberculosis*," *Antimicrobial Agents and Chemotherapy* 40(12):2809 (1996).
Klemens et al., "Activity of KRM-1648 in Comination with Isoniazid Against *Mycobacterium tuberculosis* in a Murine Model," *Antimicrobial Agents and Chemotherapy* 40(2):298 (1996).
Lenaerts et al., "Evaluation of Rifalazil in a Combination Treatment Regimen as an Alternative to Isoniazid-Rifampin Therapy in a Mouse Tuberculosis Model," *Antimicrobial Agents and Chemotherapy* 44(11):3167 (2000).
Mae et al., "Effect of a New Rifamycin Derivative, Rifalazil, on Liver Microsomal Enzyme Induction in Rat and Dog," *Xenoblotica* 28(8):759 (1998).
Mae et al., "Isolation and Identification of Major Metabolites of Rifalazil in Mouse and Human," *Xenobiotica* 29:1073 (1999).
Roblin et al., "In Vitro Activities of Rifamycin Derivatives ABI-1648 (Rifazil, KRM-1648), ABI-1657, and ABI-1131 Against *Chlamydia trachomatis* and Recent Clinical Isolates of *Chlamydia pneumoniae*," *Antimicrobial Agents and Chemotherapy* 47:1135 (2003).
Sano et al., "Therapeutic Effects of Benzoxazinorifamycin KRM-1648 Administered Alone or in Combination with a Half-sized Secretory Leukocyte Protease Inhibitor or the Nonsteroidal Anti-inflammatory Drug Diclofenac Sodium against *Mycobacterium avium* Complex Infection in Mice," *Antimicrobial Agents and Chemotherapy* 43(2):360 (1999).

(Continued)

*Primary Examiner* — Phyllis G. Spivack
(74) *Attorney, Agent, or Firm* — David Bradin; Steven J. Hultquist; Hultquist IP (57) ABSTRACT

The invention features low-dosage rifalazil compositions which are useful for the treatment of bacterial infections.

4 Claims, 7 Drawing Sheets

OTHER PUBLICATIONS

Sato et al., "Antimicrobial Activities of Benzoxazinorifamycin KRM-1648, Clarithromycin and Levofloxacin Against Intracellular *Mycobacterium avium* Complex Phagocytosed by Murine Peritoneal Macrophages," *Journal of Antimicrobial Chemotherapy* 41(1):77 (1998).

Shimizu et al., "Effects of the Chinese Traditional Medicine Mao-bushi-saishin-to on Therapeutic Efficacy of a New Benzoxazinorifamycin, KRM-1648, Against *Mycobacterium avium* Infection in Mice," *Antimicrobial Agents and Chemotherapy* 43(3):514 (1999).

Shoen et al., "Evaluation of Rifalazil in Long-term Treatment Regimens for Tuberculosis in Mice," *Antimicrobial Agents and Chemotherapy* 44(6): 1458 (2000).

Tomioka et al., "Effects of Benzoxazinorifamycin KRM-1648 on Cytokine Production at Sites of *Mycobacterium avium* Complex Infection Induced in Mice," *Antimicrobial Agents and Chemotherapy* 41(2):357 (1997).

Tomioka et al., "In Vivo Antileprosy Activity of the Newly Synthesized Benzoxazinorifamycin, KRM-1648," *International Journal of Leprosy* 61:255-258 (1993).

Tomioka et al., "Therapeutic Efficacy of KRM-1648 in Combination with Other Antimicrobials Against *M. leprae* Infection Induced in Nude Mice," *International Journal of Leprosy and Other Mycobacterial Diseases* 61:77A (1993).

Tomioka et al., "Intramacrophage Passage of *Mycobacterium tuverculosis* and *M. avium* Complex Alters the drug susceptibilities of te organisms as determined by intracellular Suseptivility Testing using Macrophages and Type II Alveolar Epithelial Cells," *Antimicrobial Agents and Chemotherapy* 46:519 (2002).

Wallis et al., "Inhibition of Isoniazid-induced Expression of *Mycobacterium tuberculosis* Antigen 85 in Sputum: Potential Surrogate Marker in Tuberculosis Chemotherapy Trials," *Antimicrobial Agents and Chemotherapy* 45(4):1302 (2001).

Yamamoto et al., "In Vitro Bactericidal and in Vivo Therapeutic Activities of a New Rifamycin Derivative, KRM-1648, Against *Mycobacterium tuberculosis*," *Antimicrobial Agents and Chemotherapy* 40(2):426 (1996).

Yamamoto et al., "Activity of KRM-1648 Alone or in Combination with Both Ethambutol and Kanamycin or Clanthromycin Against *Mycobacterium intracellulare* Infections in Beige Mice," *Antimicrobial Agents and Chemotherapy* 40(2):429 (1996).

* cited by examiner

TWO-COMPARTMENT OPEN MODEL

LOW DOSE RIFALAZIL COMPOSITIONS

CROSS-REFERENCE TO RELATED APPLICATIONS

The application claims benefit of U.S. Provisional Application No. 60/412,958 filed Sep. 23, 2002, which is incorporated herein by reference.

BACKGROUND OF THE INVENTION

The present invention relates to the field of antimicrobial therapy.

Rifalazil, an ansamycin-class antibiotic, has been described in the U.S. Pat. No. 4,983,602, where its antibacterial activity has been disclosed. Dosages described in vitro and in mice animal models correspond to a dose from 10 mg per day to 10 g per day for adults. However, when clinical trials with these doses of the antibiotic were administered daily, many adverse reactions occurred and the treatment with rifalazil was discontinued.

More recently, a once or twice-a-week dosing regimen for rifalazil was found to be efficacious against mycobacterium species, as described in U.S. Pat. No. 6,316,433. This regimen included doses ranging from 1 to 100 mg of rifalazil once or twice weekly. This dosing regimen reduced, but did not eliminate, the incidence of adverse reactions, which include the development of headaches, fevers, and "flu-like" symptoms.

SUMMARY OF THE INVENTION

We have discovered that, when administered at low doses, rifalazil resides in tissues an unexpectedly long time. As a result, therapeutically useful concentrations of rifalazil can be obtained by administering a low-dosage regimen. Such regimens may reduce the risk of adverse reactions.

In one aspect, the invention features a pharmaceutical composition containing a unit dosage form of rifalazil in an amount between 0.01 and 5 mg. Desirably, the unit dosage form contains between 0.1 and 5, 0.1 and 4, 0.1 and 3, 0.1 and 2.6, 0.1 and 2.2, 0.1 and 1.6, 0.1 and 1.2, 0.1 and 1, 0.2 and 0.8, 0.2 and 0.7, 0.01 and 4.8, 0.01 and 4, 0.01 and 3, or 0.05 and 4.8 mg of rifalazil. The unit dosage form can be a tablet, pill, capsule, or caplet, among others.

The invention further features a method of treating a bacterial infection in a patient. The method includes the step of administering to a patient any of the pharmaceutical compositions described above in an amount effective to treat the infection.

The invention also features a method of treating a bacterial infection by administering a low-dosage rifalazil regimen. The low-dosage regimen includes the step of administering to a patient between 0.01 and 10 mg of rifalazil over a period of four to fourteen days. Desirably, between 0.1 and 10, 0.01 and 8, 0.01 and 6, 0.05 and 8, 0.05 and 6, 0.1 and 5, 0.1 and 4, 0.1 and 3, 0.1 and 2.6, or 0.2 and 2.0 mg of rifalazil is administered over a period of five to ten days, or over a period of seven days.

The invention also features a method of treating a bacterial infection by administering rifalazil daily. This method includes the step of administering to a patient between 0.01 and 5 mg of rifalazil daily over a period of at least 2 days. Desirably, between 0.1 and 4, 0.1 and 4, 0.1 and 3, 0.1 and 2.6, 0.1 and 1.8, 0.01 and 4, 0.05 and 4.6, 0.05 and 4, or 0.1 and 1.6 mg of rifalazil is administered daily for a period of at least 2, 3, 4, 5, 6, 7, 8, 9, 10, 15, 20, 25, 30, 40, 50, 60, or 90 days.

The invention further features a method of treating a bacterial infection by administering rifalazil in a loading-dose regimen. The loading-dose regimen can include: (i) an initial administration of rifalazil at an average daily dose for 4 to 14 days, followed by less than half this average daily dose for the subsequent following 4 to 14 days; (ii) an average initial daily dose of rifalazil which is at least 200% of the average daily dose over two, three, four, or five subsequent dosing days; or (iii) administering rifalazil at a dose administered on Day 1 that is at least 200% of the dose administered on any of the next four dosing days.

The loading-dose regimen described above includes the step of administering to the patient an average initial daily dose of between 4.5 and 200, 4.5 and 100, 4.5 and 50, 4.5 and 40, 4.5 and 30, 4.5 and 20, 4.5 and 15, 5 and 14, 5 and 12, or 5 and 10 mg/day of rifalazil. Following the initial daily dose, maintenance doses of rifalazil are given to the patient to sustain a desired tissue concentration of rifalazil in the patient. The maintenance doses are greater than 0.01 mg of rifalazil per week. The maintenance doses can be administered as a low-dosage or daily regimen described herein.

Any of the methods and compositions described above are useful for the treatment of community-acquired pneumonia, upper and lower respiratory tract infections, skin and soft tissue infections, hospital-acquired lung infections, bone and joint infections, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, central nervous system infections, bacteremia, wound infections, peritonitis, meningitis, infections after burn, urogenital tract infections, gastro-intestinal tract infections, pelvic inflammatory disease, endocarditis, and other intravascular infections. The infections to be treated may be caused by Gram-positive bacteria. These include, without limitation, infections by, *Staphylococcus aureus, Staphylococcus epidermidis, Enterococcus faecalis, Enterococcus faecium, Clostridium perfringens, Clostridium difficile, Streptococcus pyogenes, Streptococcus pneumoniae*, other *Streptococcus* spp., and other *Clostridium* spp. More specifically, the infections may be caused by a Gram-positive coccus, or by a drug-resistant Gram-positive coccus. Exemplary Gram-positive cocci are, without limitation, *S. aureus, S. epidermidis, S. pneumoniae, S. pyogenes, M. catarrhalis, C. difficile, H. pylori, Chlamydia* spp., and *Enterococcus* spp.

The methods and compositions described above can be used to reduce or eliminate the incidence of postoperative infections in patients undergoing surgical procedures or implantation of prosthetic devices.

Furthermore, the methods and compositions described herein are useful for treating an infection by multi-drug resistant bacteria. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the invention include, for example, infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

The invention features a method for treating a patient diagnosed as being infected with a bacterium having a multiplying form and a non-multiplying form. This method includes the step of administering to the patient (i) a unit dosage form, low-dosage regimen, or loading-dose regimen of rifalazil described herein, and (ii) a second antibiotic that is effective against the multiplying form of the bacterium, wherein the two antibiotics are administered in amounts and for a duration that together treat the patient.

In one preferred method of carrying out the foregoing method, the antibiotic that is effective against the multiplying form of the bacterium is administered in an amount and for a duration to reduce the number of bacteria in the patient to less than about $10^6$ organisms/mL. This typically takes from a few hours to one, two or three days, but may take as long as a week. After this has been achieved, the patient is then administered a unit dosage form, low-dosage regimen, or loading-dose regimen of rifalazil described herein in an amount and for a duration effective to complete the treatment of the patient. Antibiotics that are effective against the multiplying form of the bacterium include any of the antibiotics described herein.

The invention features a method for treating a human patient diagnosed as having a chronic disease associated with a bacterial infection caused by bacteria capable of establishing a cryptic phase. The method includes the step of administering a unit dosage form, low-dosage regimen, or loading-dose regimen of rifalazil described herein to the patient.

The invention features a method for treating the cryptic phase of a bacterial infection. This method includes the step of administering a unit dosage form, low-dosage regimen, or loading-dose regimen of rifalazil described herein to a patient. The administering is for a time and in an amount effective to treat the cryptic phase of the bacterial infection.

The invention features a method for treating a bacterial infection in a human patient by (a) treating the multiplying form of the bacteria by administering an antibiotic to the patient for a time and an amount sufficient to treat the multiplying form, and (b) treating the non-multiplying form of the bacteria by administering a unit dosage form, low-dosage regimen, or loading-dose regimen of rifalazil described herein to the patient, wherein the administering is for a time and in an amount effective to treat the non-multiplying form.

Preferably, the bacterial infection is caused by one of the following: Chlamydia spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. negevensis,* or *P. acanthamoeba*.

The time effective to treat a cryptic phase or other non-multiplying form of a bacterium ranges from one day to one year. In certain instances, treatment can be for several weeks or months, or even extended over the lifetime of the individual patient, if necessary. For example, the duration of treatment may be at least 30 days, at least 45 days, at least 90 days, or at least 180 days. Ultimately, it is most desirable to extend the treatment for such a time that the non-multiplying form is no longer detectable.

The invention features a method for treating or preventing the development of an atherosclerosis-associated disease in a human patient. The method includes administering a unit dosage form, low-dosage regimen, or loading-dose regimen of rifalazil described herein to the patient, wherein the administering is for a time and in an amount effective to treat or prevent the development of the atherosclerosis-associated disease in the patient. The patient is typically diagnosed as having the atherosclerosis-associated disease (or being at increased risk of developing the disease) or as having macrophages or foam cells infected with *C. pneumoniae* prior to a low-dosage administration of rifalazil.

The invention also features a method of reducing the level of C-reactive protein in a human patient in need thereof. This method includes administering a unit dosage form, low-dosage regimen, or loading-dose regimen of rifalazil described herein to the patient, wherein the administering is for a time and in an amount effective to reduce the level of C-reactive protein in the patient. In one embodiment, the patient has not been diagnosed as having a bacterial infection. In another embodiment, the patient has been diagnosed as having macrophages or foam cells infected with *C. pneumoniae*.

The invention features a method for reducing *C. pneumoniae* replication in macrophages or foam cells in a human patient in need thereof. This method includes administering a unit dosage form, low-dosage regimen, or loading-dose regimen of rifalazil described herein to the patient, wherein the administering is for a time and in an amount effective to reduce *C. pneumoniae* replication in macrophages or foam cells in the patient.

The invention also features a method for treating a persistent *C. pneumoniae* infection in macrophages or foam cells in a human patient. The method includes administering a unit dosage form, low-dosage regimen, or loading-dose regimen of rifalazil described herein to the patient, wherein the administering is for a time and in an amount effective to treat the *C. pneumoniae* infection in macrophages or foam cells in the patient.

The invention also features a method for treating a chronic disease associated with an infection of *C. pneumoniae*. The method includes administering a unit dosage form, low-dosage regimen, or loading-dose regimen of rifalazil described herein to the patient, wherein the administering is for a time and in an amount effective to treat the infection.

The invention further features a method for treating a human patient having antibiotic-associated bacterial diarrhea or an infection of *C. difficile*, or preventing the disease or infection in the patient. The method includes administering a unit dosage form, low-dosage regimen, or loading-dose regimen of rifalazil described herein to the patient, wherein the administering is for a time and in an amount effective to treat the infection. The method may be employed as an initial treatment of a patient having or being at risk for developing antibiotic-associated bacterial diarrhea or infection of *C. difficile*, or it may be employed to treat patients for whom the initial treatment (e.g., with metronidazole or vancomycin) has failed to fully treat the antibiotic-associated bacterial diarrhea or an infection of *C. difficile*. The method may be employed, for example, when the patient is colonized with *C. difficile* organisms that are resistant to one or more of metronidazole, vancomycin, and rifampicin.

For any of the methods described herein, rifalazil may be administered in conjunction with one or more additional agents such as anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) and steroids (e.g., cortisone, dexamethasone, hydrocortisone, methylprednisolone, prednisolone, prednisone, triamcinolone)), antibacterial agents (e.g., aminoglycosides, amphenicols, ansamycins, β-Lactams, carbapenems, cephalosporins, cephamycins, lincosamides, macrolides, polypeptides, tetracyclines, 2,4-diaminopyrimidines, nitrofurans, quinolones, sulfonamides, lipopeptides, oxazolidones, ketolides, or sulfones. Exemplary antibiotics include amikacin, gentamicin, kanamycin, tetracycline, vancomycin, teicoplanin, azithromycin, clarithromycin, erythromycin, gatifloxacin, levofloxacin, amoxicillin, and metronidazole), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, and fluvastatin). These additional agents may be administered within 14 days, 7 days, 1 day, 12 hours, or 1 hour of the low-dosage administration of rifalazil, or simultaneously therewith. The additional therapeutic agents may be present in the same or different pharmaceutical compositions as the formulation of rifalazil. When present in different pharmaceutical compositions, different routes of administration may be used. For example, a second agent may be administered orally or by intramuscular or subcutaneous injection. Agents that can be administered in conjunction with rifalazil include any of the agents described herein.

The invention features a method for treating a patient having an infection of *Chlamydia* (*C.*) *trachomatis* or a disease due to an infection of *C. trachomatis*. The method includes the step of administering to the patient a single oral dose of rifalazil. Sexually transmitted diseases caused by *C. trachomatis* include, without limitation, urethritis, cervicitis, salpingitis, endometritis, epididymitis, lymphogranuloma venereum, proctitis, perihepatitis, and trachoma. The single oral dose of rifalazil is between 0.01 and 100 mg of rifalazil. Desirably, between 0.01 and 50, 0.01 and 25, 0.01 and 10, 0.01 and 5, 0.1 and 25, 0.1 and 10, 0.5 and 15, or 5 and 25 mg of rifalazil is administered in a single oral dose. The method also includes administering a unit dosage form of rifalazil described herein. Accordingly, between 0.01 and 5, 0.1 and 5, 0.1 and 4, 0.1 and 3, 0.1 and 2.5, 0.25 and 5, 0.25 and 4, 1 and 5, 1 and 4, 1 and 3, 0.5 and 4, 0.5 and 3, or 0.5 and 2 mg of rifalazil is administered as a single oral dose to treat the disease or infection caused by *C. trachomatis*.

The invention further features a pharmaceutical formulation including rifalazil. The formulation is packaged with a label or package insert providing instructions for the use of the formulation wherein the instructions describe administration of rifalazil in a loading-dose regimen.

The pharmaceutical formulation may be a prepackaged therapeutic regimen including a first dosage unit which includes rifalazil; a second dosage unit which includes a smaller dose of rifalazil than the first dosage unit; instructions for the administration of the first dosage unit prior to the second dosage unit; and a pharmaceutical dispensing container prefilled with the dosage units and incorporating the instructions.

The dosage units may include one or more tablets, pills, capsules, or caplets. Desirably, the second dosage unit contains rifalazil in an amount between 0.01 and 5 mg per unit. Desirably, the second dosage unit contains rifalazil in an amount between 0.1 and 5, 0.1 and 4, 0.1 and 3, 0.1 and 2.5, 0.25 and 5, 0.25 and 4, 1 and 5, 1 and 4, 1 and 3, 0.05 and 4, 0.05 and 3, or 0.05 and 2 mg per unit.

The container can have one of any number of forms, including, without limitation, a box with the dosages in bottles, a blister package, a box of individual blister packages, or a box of pouches.

The term "unit dosage forms" refers to physically discrete units suitable as unitary dosages for human subjects, each unit containing a predetermined quantity of rifalazil in amounts of less than 5 milligrams but sufficient to produce the desired therapeutic effect, in association with a suitable pharmaceutical excipient.

As used herein, when "between" refers to a range of values, the upper and lower limits recited define the outside boundaries of the range, but are not included in the range.

By "low-dosage regimen" is meant a regimen for the administration of rifalazil to a patient, wherein between 0.01 and 10 mg of rifalazil is administered over a period of four to fourteen days.

In some embodiments, the low-dosage regimen includes between 0.1 and 10, 0.01 and 8, 0.01 and 6, 0.1 and 5, 0.1 and 4, 0.1 and 3, 0.1 and 2.6, or 0.2 and 2 mg of rifalazil administered over a period of five to ten days, or over a period of seven days.

By "loading-dose regimen" is meant a regimen for the administration of rifalazil that includes at least two administrations of rifalazil in which any of the following criteria are met: i) the average daily dose administered from the first day of treatment to day 4 is at least 200% of the average daily dose administered over the subsequent following four to fourteen days of administration; ii) the average initial daily dose is at least 200% of the average daily dose over five subsequent dosing days; or iii) the dose administered on Day 1 is at least 200% of the dose administered on any of the next four dosing days.

In some embodiments, the loading-dose regimen includes an average daily dose administered from the first day of treatment to 4, 6, 8, 10, 12, or 14 days which is at least 200%, 250%, 300%, 350%, 400%, 500%, 600%, or 700% of the average daily dose administered over the following four to fourteen days of administration; a regimen in which the average initial daily dose is at least 200%, 250%, 300%, 350%, 400%, 500%, 600%, or 700% of the average daily dose over two, three, four, or five subsequent dosing days; or a regimen in which the dose administered on Day 1 is at least 200%, 250%, 300%, 350%, 400%, 500%, 600%, or 700% of the dose administered on any of the next four dosing days.

By "average daily dose" is meant the administered dose, in milligrams, of rifalazil per unit time. The average daily dose is calculated from the instructed regimen. For example, 25 mg twice weekly is an average daily dose of 7.14 mg/day (50 mg/7 days); 15 mg once in week 1 followed by 1 mg daily in week 2 is an average daily dose in week 1 of 2.14 mg/day (15 mg/7 days) and in week 2 of 1.0 mg/day (7 mg/7 days). For regimens of indefinite intervals, the average daily dose is calculated from the average of the high and low values. For example, a regimen that calls for 15 mg over seven to ten days has an average daily dose of 1.82 mg/day {(15 mg/7 days+15 mg/10 days)/2}.

By "average initial daily dose" is meant the dose of rifalazil administered on Day 1 divided by the time until the next administration. For example, a dosing regimen that calls for administration of 10 mg of rifalazil on Day 1, followed by 2.5 mg on days 8, 10, 14, and 18, has an average initial daily dose of 1.43 mg/day {10 mg/(8-1)}.

By "average daily dose over N subsequent dosing days" is meant the sum of rifalazil administered in N dosing days subsequent to the day of the initial administration divided by the time over which N+1 dosing days subsequent to the initial administration are made. For example, a dosing regimen that calls for administration of 10 mg of rifalazil on Day 1, followed by 2.5 mg on days 8, 10, 14, 18, 23, and 27, has an average daily dose over three subsequent dosing days of 0.75 mg/day {(2.5+2.5+2.5)/(18-8)}; an average daily dose over four subsequent dosing days of 0.66 mg/day {(2.5+2.5+2.5+

2.5)/(23-8)}; and an average daily dose over five subsequent dosing days of 0.66 mg/day {(2.5+2.5+2.5+2.5+2.5)/(27-8)}.

By "initial administration" is meant administration of rifalazil to a patient to whom rifalazil has not been administered in the previous 15 days. Desirably, the rifalazil has not been administered in the previous 22 days, 1 month, 2 months, or 3 months.

By "dose administered on Day 1" is meant the sum total of all rifalazil administered over the first 24 hours of the initial administration.

By "dosing day" is meant a day on which a rifalazil is administered to a patient to whom rifalazil has not been administered in the previous 24 hours, wherein the dose administered on a dosing day is the sum total of all rifalazil administered over a 24 hour period beginning from the first administration on this day.

As used herein, the term "treating" refers to administering a pharmaceutical composition for prophylactic and/or therapeutic purposes. To "prevent disease" refers to prophylactic treatment of a human patient who is not yet ill, but who is susceptible to, or otherwise at risk of, a particular disease. To "treat disease" or use for "therapeutic treatment" refers to administering treatment to a patient already suffering from a disease to improve or stabilize the patient's condition. Thus, in the claims and embodiments, treating is the administration to a human patient either for therapeutic or prophylactic purposes.

As used herein, the term "administration" or "administering" refers to a method of giving an oral dosage of a pharmaceutical composition to a human patient.

By "effective" amount is meant the amount of rifalazil required to treat or prevent an infection or a disease associated with an infection. The effective amount of rifalazil used to practice the invention for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective" amount.

By "bacterial infection" is meant the invasion of a host by pathogenic bacteria. For example, the infection may include the excessive growth of bacteria that are normally present in or on the body of a patient or growth of bacteria that are not normally present in or on a human. More generally, a bacterial infection can be any situation in which the presence of a bacterial population(s) is damaging to a host body. Thus, a human is "suffering" from a bacterial infection when an excessive amount of a bacterial population is present in or on the person's body, or when the presence of a bacterial population(s) is damaging the cells or other tissue of the person.

By "atherosclerosis" is meant the progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A human patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, incorporated herein by reference. Diagnosis and monitoring may employ an electrocardiogram, chest X-ray, echocardiogram, cardiac catheterization, ultrasound (for the measurement of vessel wall thickness), or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic low-dosage administration of rifalazil is considered to be preventing the development of an atherosclerosis-associated disease.

An atherosclerosis-associated disease has been treated or prevented when one or more tests of the disease (e.g., any of the those described above) indicate that the patient's condition has improved or the patient's risk reduced. In one example, a reduction in C-reactive protein to normal levels indicates that an atherosclerosis-associated disease has been treated or prevented.

An alternative means by which treatment or prevention is assessed includes determination of the presence of an infection of *C. pneumoniae*. Any suitable method may be employed (e.g., determination of *C. pneumoniae* in blood monocytes or in the atheroma itself (e.g., in macrophages or foam cells present in the fatty streak), or detection of *C. pneumoniae* DNA, RNA, or antibodies to *C. pneumoniae* in a biological sample from the patient).

"Antibiotic-associated bacterial diarrhea" means the condition wherein antibiotic therapy disturbs the balance of the microbial flora of the gut, allowing pathogenic organisms such as *C. difficile* to flourish. These organisms cause diarrhea. Antibiotic-associated bacterial diarrhea includes such conditions as *C. difficile* associated diarrhea (CDAD) and pseudomembranous colitis. When rifalazil is administered at a low dosage for the treatment of a *C. difficile* infection, an effective amount of rifalazil is the amount required to eradicate *C. difficile* from the patient, or the amount which prevents an infection of *C. difficile*, as determined by a diagnostic test that detects *C. difficile*.

"Pseudomembranous colitis," also known as pseudomembranous enterocolitis or enteritis, means the inflammation of the mucous membrane of both small and large intestine with the formation and passage of pseudomembranous material (composed of fibrin, mucous, necrotic epithelial cells and leukocytes) in the stools.

The term "lower gastrointestinal tract" means the lower part of the small intestine (ileum) and the colon.

By "autoimmune disease" is meant a disease arising from an immune reaction against self-antigens and directed against the individual's own tissues. Examples of autoimmune diseases include but are not limited to systemic lupus erythematosus, rheumatoid arthritis, myasthenia gravis, and Graves' disease.

By "bacteria" is meant a unicellular prokaryotic microorganism that usually ultiplies by cell division.

By "bacteria capable of establishing a cryptic phase" is meant any species hose life cycle includes a persistent, non-multiplying phase. These species include but are not limited to C. trachomatis, C. pneumoniae, C. psittaci, C. suis, C. pecorum, C. abortus, C. caviae, C. felis, C. muridarum, N. hartmannellae, W. chondrophila, S. negevensis, and P. acanthamoeba, as well as any other species described in Everett et al. (Int. J. Syst. Evol. Microbiol. 49:415-440, (1999)).

By "chronic disease" is meant an inveterate disease of long continuance, or which progresses slowly, in contrast to an acute disease, which rapidly terminates. A chronic disease may begin with a rapid onset or in a slow insidious manner but it tends to persist for several weeks, months or years, and has a vague and indefinite termination.

By "cryptic phase" is meant the latent or dormant intracellular phase of infection characterized by little or no metabolic activity. The non-replicating cryptic phase is often characteristic of persistent forms of intracellular bacterial infections.

By "elementary body phase" is meant the infectious phase of the bacterial life cycle which is characterized by the presence of elementary bodies (EBs). EBs are small (300-400 nm), infectious, spore-like forms which are metabolically inactive, non-replicating, and found most often in the acellular milieu. EBs possess a rigid outer membrane which protects them from a variety of physical insults such as enzymatic degradation, sonication and osmotic pressure.

By "immunocompromised" is meant a person who exhibits an attenuated or reduced ability to mount a normal cellular or humoral defense to challenge by infectious agents, e.g., viruses, bacterial, fungi, and protozoa. Persons considered immunocompromised include malnourished patients, patients undergoing surgery and bone narrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory disease include asthma, coronary artery disease, arthritis, conjunctivitis, lymphogranuloma venerum, and salpingitis.

By "intracytoplasmic inclusion" is meant a replicating reticulate body (RB) that has no cell wall. Such inclusions may be detected, for example, through chlamydiae sample isolation and propagation on a mammalian cell lines, followed by fixing and staining using one of a variety of staining methods including Giemsa staining, iodine staining, and immunofluorescence. These inclusions have a typical round or oval appearance.

By "persistent bacterial infection" is meant an infection that is not completely eradicated through standard treatment regimens using antibiotics. Persistent bacterial infections are caused by bacteria capable of establishing a cryptic phase or other non-multiplying form of a bacterium and may be classified as such by culturing bacteria from a patient and demonstrating bacterial survival in vitro in the presence of antibiotics or by determination of anti-bacterial treatment failure in a patient. As used herein, a persistent infection in a patient includes any recurrence of an infection, after receiving antibiotic treatment, from the same species more than two times over the period of two or more years or the detection of the cryptic phase of the infection in the patient. An in vivo persistent infection can be identified through the use of a reverse transcriptase polymerase chain reaction (RT-PCR) to demonstrate the presence of 16S rRNA transcripts in bacterially infected cells after treatment with one or more antibiotics (Antimicrob. Agents Chemother. 12:3288-3297, (2000)).

As used herein, "non-multiplying" phase or bacteria refers to the non-multiplying growth phase of bacteria. Typically, the non-multiplying bacteria will survive standard antimicrobial therapy (see, e.g., Martinez et al., Antimicrob. Agents Chemother. 44:1771-1777 (2000); Riesenfeld et al., Antimicrob. Agents Chemother. 41:2059-2060 (1997); Alonso et al., Microbiology 145:2857-2862 (1999)).

By "replicating phase" is meant the phase of the bacterial cell cycle characterized by the presence of an RB. The RB is the actively replicating form of the Chlamydia. It contains no cell wall and is detected as an inclusion in the cell.

The term "microbial infection" refers to the invasion of the host patient by pathogenic microbes. This includes the excessive growth of microbes that are normally present in or on the body of a patient. More generally, a microbial infection can be any situation in which the presence of a microbial population(s) is damaging to a host patient. Thus, a patient is "suffering" from a microbial infection when excessive numbers of a microbial population are present in or on a patient's body, or when the presence of a microbial population(s) is damaging the cells or other tissue of a patient.

While the invention is described herein in terms of rifalazil, the invention applies as well to rifalazil analogs. Analogs of rifalazil are compounds that satisfy formula (I):

In formula I, $X^1$ represents an oxygen atom or a sulfur atom, $R^2$ represents a hydrogen, a hydroxyl group, or an alkyl group having 1 to 3 carbons, $R^1$ represents a hydrogen or an acetyl group, and $R^3$ represents a hydrogen atom or a group expressed by the formula:

wherein each of $R^4$ and $R^5$ is, independently, an alkyl group having 1 to 6 carbon atoms, or $R^4$ and $R^5$ combine to form a 3-8 membered cyclic system,
or $R^3$ represents a group expressed by the formula:

in which g represents an integer between 1 and 3;
or $R^3$ represents a group expressed by the formula:

wherein each of $R^6$ and $R^7$ is, independently, a hydrogen atom or an alkyl group having 1 to 3 carbon atoms, $X^2$ represents an oxygen atom, a sulfur atom, or a carbonyl group,
or $X^2$ represents a group expressed by the formula:

in which each of $R^8$ and $R^9$ is, independently, a hydrogen atom, or an alkyl group having 1 to 3 carbon atoms, or $R^8$ and $R^9$, in combination with each other, represent —$(CH_2)_k$— in which k represents an integer between 1 and 4;
or $X^2$ represents a group expressed by the formula:

in which m represents 0 or 1, $R^{10}$ represents a hydrogen atom, an alkyl group having 1 to 6 carbon atoms, or —$(CH_2)_n X^3$ in which n represents an integer between 1 and 4, and $X^3$ represents an alkoxy group having 1 to 3 carbon atoms, a vinyl group, an ethynyl group,
or $X^2$ represents a group expressed by the formula:

In formula (I), each of the alkyl groups having 1 to 3 carbon atoms expressed by $R^2$, $R^6$, $R^7$, $R^8$, and $R^9$ are each, independently, selected from methyl, ethyl, propyl, isopropyl, and cyclopropyl. The alkyl group having 1 to 6 carbon atoms expressed by $R^4$, $R^5$, and $R^{10}$ are each, independently, selected from a chain or cyclic alkyl group, examples of which include, without limitation, methyl, ethyl, propyl, isopropyl, cyclopropyl, butyl, isobutyl, sec-butyl, tert-butyl, cyclobutyl, cyclopropylmethyl, pentyl, isopentyl, sec-pentyl, tert-pentyl, cyclopentyl, cyclobutylmethyl, hexyl, 4-methylpentyl, cyclohexyl, 3-methylcyclopentyl, among others. The alkoxy group having 1 to 3 carbon atoms expressed by $X^3$ is selected from methoxy, ethoxy, propoxy, isopropoxy, and cyclopropoxy. Analogs of rifalazil include those compounds disclosed in U.S. Pat. Nos. 4,690,919, 4,859,661, 4,983,602, 5,786,349, and 5,981,522, each of which is incorporated herein by reference.

DETAILED DESCRIPTION

The invention provides rifalazil compositions and therapeutic regimens which are useful for the treatment of bacterial infections.

The therapeutic regimen can be a low-dosage regimen, in which rifalazil is administered to a patient in an amount between 0.1 and 10 mg over a period of four to fourteen days, a daily regimen, in which rifalazil is administered to a patient in a daily amount of between 0.1 and 5 mg over a period of one to sixty days, or a loading-dose regimen. The loading-dose regimen, described above, includes the step of administering to the patient an average initial daily dose of between 4.5 and 200 mg/day of rifalazil. Following the initial daily dose, maintenance doses of rifalazil are given to the patient to sustain a desired tissue concentration of rifalazil in the patient. For example, the maintenance doses can themselves be a low-dosage or daily regimen.

These therapeutic regimens can be useful for the treatment of community-acquired pneumonia, upper and lower respiratory tract infections, skin and soft tissue infections, hospital-acquired lung infections, bone and joint infections, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, central nervous system infections, bacteremia, wound infections, peritonitis, meningitis, infections after burn, urogenital tract infections, gastro-intestinal tract infections, pelvic inflammatory disease, intravascular infections, such as endocarditis, and any other infection or infection related disease described herein.

Other Therapeutic Agents

Rifalazil formulations and compositions described herein may also include a second therapeutic agent, including for example, another antibiotic, an anesthetic, an antimicrobial agent, a zinc salt, or an anti-inflammatory agent (e.g., an non-steroidal anti-inflammatory or a steroid).

Antibiotics that can be admixed with the low-dosage rifalazil formulation include: aminoglycosides, such as amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin; amphenicols, such as azidamfenicol, chloramphenicol, chloramphenicol palmirate, chloramphenicol pantothenate, florfenicol, and thiamphenicol; ansamycins, such as rifampin, rifabutin, rifapentine, and rifaximin; β-Lactams, such as amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin; carbapenems, such as imipenem; cephalosporins, such as 1-carba (dethia) cephalosporin, cefactor, cefadroxil, cefamandole, cefatrizine, cefazedone, cefazolin, cefixime, cefinenoxime, cefodizime, cefonicid, cefoperazone, cefo­ranide, cefotaxime, cefotiam, cefpimizole, cefpirimide, cef­podoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, and cefepime; cephamycins such as cefbuperazone, cefinetazole, cefminox, cefetan, and cefoxitin; monobactams such as aztreonam, carumonam, and tigemonan; oxacephems such as flomoxef and moxolactam; lincosamides such as clindamycin and lincomycin; macrolides such as azithromycin, carbomycin, clarithromycin, erythromycin(s) and derivatives, josamycin, leucomycins, midecamycins, miokamycin, oleandomycin, primycin, rokitamycin, rosaramicin, roxithromycin, spiramycin and troleandomycin; polypeptides such as amphomycin, bacitracin, capreomycin, colistin, enduracidin, enylomycin, fusafungine, gramicidin(s), gramicidin S, mikamycin, polymyxin, polymyxin β-methanesulfonic acid, pristinamycin, ristocetin, teicoplanin, thiostrepton, tuberactinomycin, tyrocidine, tyrothricin, vancomycin, viomycin(s), virginiamycin and zinc bacitracin; tetracyclines such as spicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline; and 2,4-diaminopyrimidines such as brodimoprim, tetroxoprim and trimethoprim; nitrofurans such as furaltadone, furazolium, nifuradene, nifuratel, nifurfoline, nifurpirinol, nifurprazine, nifurtoinol and nitrofurantoin; quinolones such as amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, perfloxacin, pipemidic acid, piromidic acid, rosoxacin, temafloxacin, and tosufloxacin; sulfonamides such as acetyl sulfamethoxypyrazine, acetyl sulfisoxazole, azosulfamide, benzylsulfamide, chloramine-β, chloramine-T, dichloramine-T, formosulfathiazole, $N_2$-formyl-sulfisomidine, $N_4$-β-D-glucosylsulfanilamide, mafenide, 4'-(methyl-sulfamoyl) sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, $N_4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole; sulfones, such as acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N, N'digalactoside, sulfoxone and thiazolsulfone; lipopeptides such as daptomycin; oxazolidones such as linezolid; ketolides such as telithromycin; and miscellaneous antibiotics such as clofoctol, hexedine, magainins, methenamine, metbenamine anhydromethylene-citrate, methenamine hippurate, methenamine mandelate, methenamine sulfosalicylate, nitroxoline, squalamine, xibornol, cycloserine, mupirocin, and tuberin.

Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine, and preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone.

Preferred anesthetics include, for example, benzocaine, butamben picrate, tetracaine, dibucaine, prilocalne, etidocaine, mepivacaine, bupivicaine, and lidocaine.

Preferred zinc salts include, for example, zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

All of the therapeutic agents employed in the compositions of the invention can be used in the dose ranges currently known and used for these agents. Different concentrations may be employed depending on the clinical condition of the patient, the goal of therapy (treatment or prophylaxis), the anticipated duration, and the severity of the infection or disease for which a low-dosage rifalazil formulation is being administered. Additional considerations in dose selection include the type of infection, age of the patient (e.g., pediatric, adult, or geriatric), general health, and comorbidity. Determining what concentrations to employ are within the skills of the pharmacist, medicinal chemist, or medical practitioner formulating the low-dosage rifalazil in combination with other therapeutic agents.

Therapy

The rifalazil compositions and therapeutic regimens described herein can be used to treat or prevent bacterial infections as well as diseases associated with bacterial infections.

Bacterial infections that can be treated or prevented include, for example, respiratory tract infections (e.g., inhalation anthrax), acute bacterial otitis media, bacterial pneumonia, urinary tract infections, complicated infections, non-complicated infections, pyelonephritis; intra-abdominal infections, deep-seated abcesses, bacterial sepsis, skin and skin structure infections (e.g., cutaneous anthrax), soft tissue infections (e.g., endometritis), bone and joint infections (e.g., osteomyelitis, septic arthritis), central nervous system infections (e.g., meningitis), bacteremia, wound infections, peritonitis, meningitis, infections after burn, urogenital tract infections, gastro-intestinal tract infections (e.g., antibiotic-associated colitis, gastrointestinal anthrax), pelvic inflammatory disease, and endocarditis.

Diseases Associated with Infections

Diseases associated with bacterial infections include, but are not limited to, atherosclerosis, multiple sclerosis, rheumatoid arthritis, diabetes, Alzheimer's disease, asthma, cirrhosis of the liver, psoriasis, meningitis, cystic fibrosis, cancer, and osteoporosis.

Several lines of evidence have led to the establishment of a link between bacterial infections and a broad set of inflammatory, autoimmune, and immune deficiency diseases. Thus, the present invention describes methods for treating chronic diseases associated with a persistent infection, such as autoimmune diseases, inflammatory diseases and diseases that occur in immuno-compromised individuals by treating the non-multiplying form of the infection in an individual in need thereof, by administering rifalazil, or rifalazil in conjunction with an antibiotic effective against multiplying bacteria. Progress of the treatment can be evaluated, using the diagnostic tests known in the art, to determine the presence or absence of the bacteria. Physical improvement in the conditions and symptoms typically associated with the disease to be treated can also be evaluated. Based upon these evaluating factors, the physician can maintain or modify the anti-bacterial therapy accordingly.

The therapies described herein can be used for the treatment of chronic immune and autoimmune diseases when patients are demonstrated to have a bacterial infection. These diseases include, but are not limited to, chronic hepatitis, systemic lupus erythematosus, arthritis, thyroidosis, scleroderma, diabetes mellitus, Graves' disease, Beschet's disease, and graft versus host disease (graft rejection). The therapies of this invention can also be used to treat any disorders in which a bacterial infection is a factor or co-factor.

Thus, the present invention can be used to treat a range of disorders in addition to the above immune and autoimmune diseases when demonstrated to be associated with chlamydial infection by the methods of detection described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated.

Among the various inflammatory diseases, there are certain features that are generally agreed to be characteristic of the inflammatory process. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis, chronic vascular headaches (including migraines, cluster headaches and tension headaches) and pneumonia when demonstrated to be pathogenically related to a bacterial infection.

Treatable disorders when associated with a bacterial infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supranucleo palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and dementia pugilistica.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or mycosis fungoides)); carcinomas (such as colon carcinoma) and metastases thereof; cancer-related angiogenesis; infantile hemangiomas; and alcohol-induced hepatitis. Ocular neovascularization, psoriasis, duodenal ulcers, and angiogenesis of the female reproductive tract, can also be treated when demonstrated to be associated with a bacterial infection.

Administration and Formulation

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 5 mg of rifalazil.

The tablets or pills of the present invention may be coated or otherwise compounded to provide a dosage form affording the advantage of prolonged action. For example, the tablet or pill can include an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the drugs used in this invention may be incorporated for administration orally include liquid-filled gelatin capsules. Liquid forms include aqueous solutions, oil solutions, aqueous or oil suspensions, alcohol solutions, and similar pharmaceutical vehicles.

Therapeutic formulations may, for example, be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of rifalazil in the formulation will vary depending upon a number of factors, including the dosage of the drug to be administered, and the route of administration.

Rifalazil may optionally be formulated as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided as chewable tablets.

Rifalazil may optionally be formulated for controlled release. Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Packaging and Instructions

The methods and compositions of the present invention can be disclosed in the form of instructions for the administration of rifalazil in a loading-dose regimen. Typically, the method is disclosed to a patient along with the sale or distribution of rifalazil. In some instances, instructions may be included on a label or on a package insert accompanying a pharmaceutical formulation containing rifalazil. The method of the present invention can be incorporated into a prepackaged therapeutic regimen designed to deliver a loading-dose regimen of rifalazil to a patient using the prepackaged regimen. For example, rifalazil can be packaged in dosage units containing varying quantities of rifalazil along with instructions to the patient to administer the larger quantities followed by the smaller quantities over a particular time period. Such doses may consist of one or more tablets, pills, capsules, or caplets.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLES

Example 1

ABI-1648-006 Clinical Trial

A clinical trial was conducted to monitor the safety and pharmacokinetics of low doses of rifalazil in humans. For these clinical studies, described below, hard gelatin capsules containing microgranulated rifalazil (as described in U.S. Pat. No. 5,547,683) were prepared at several different strengths: 2.5 mg, 5 mg, 12.5 mg, and 25 mg.

Figure 1A:
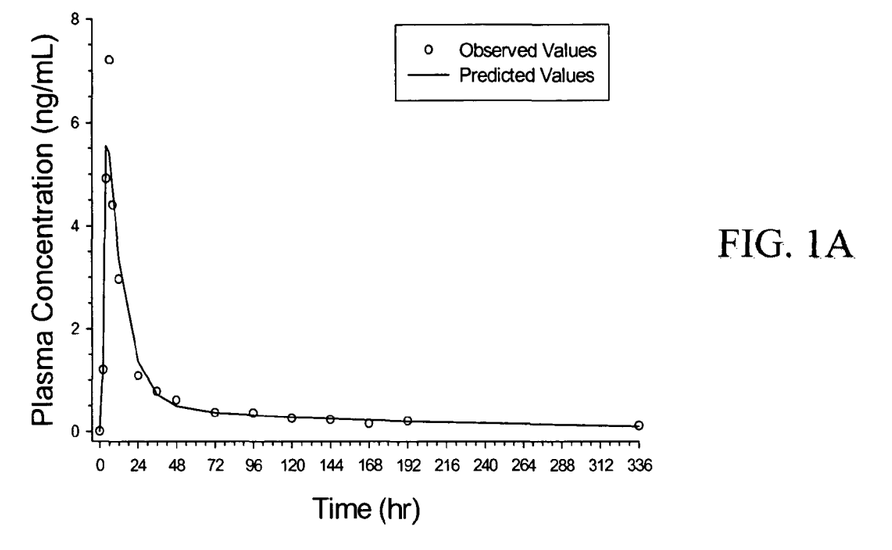
FIG. 1A is a graph depicting the observed plasma concentration of rifalazil in male subjects following the oral administration of a 2.5 mg dose of rifalazil.
Figure 1B:
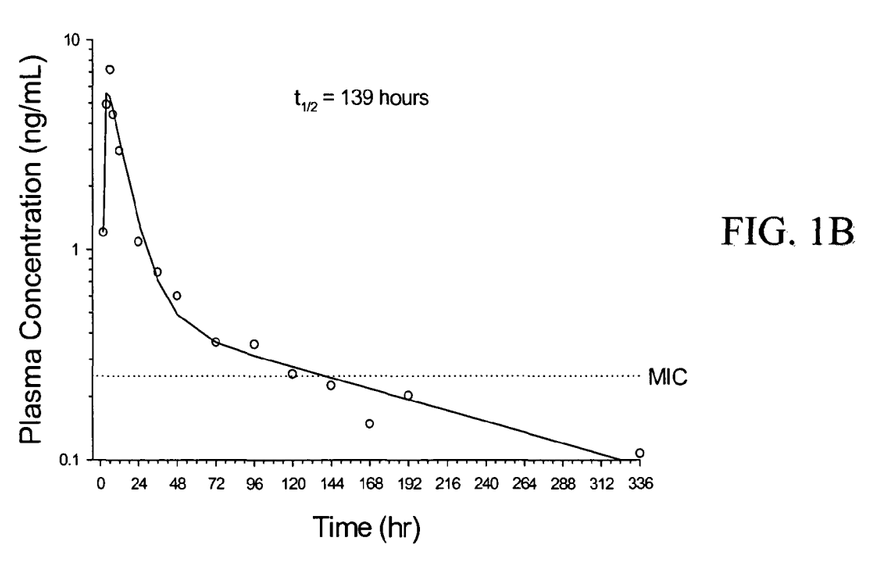
FIG. 1B is a log-graph depicting the observed plasma concentration of rifalazil in male subjects following the oral administration of a 2.5 mg dose and the point at which the plasma concentration falls below the MIC for *Chlamydia trachomatis*.

Rifalazil was administered to 80 patients in a randomized trial at single doses of 2.5 mg (see FIGS. 1A and 1B), 5 mg, 12.5 mg, and 25 mg; daily for five days at doses of 2.5 mg/day and 5 mg/day; and daily for two days at 12.5 mg/day.

Figure 2:
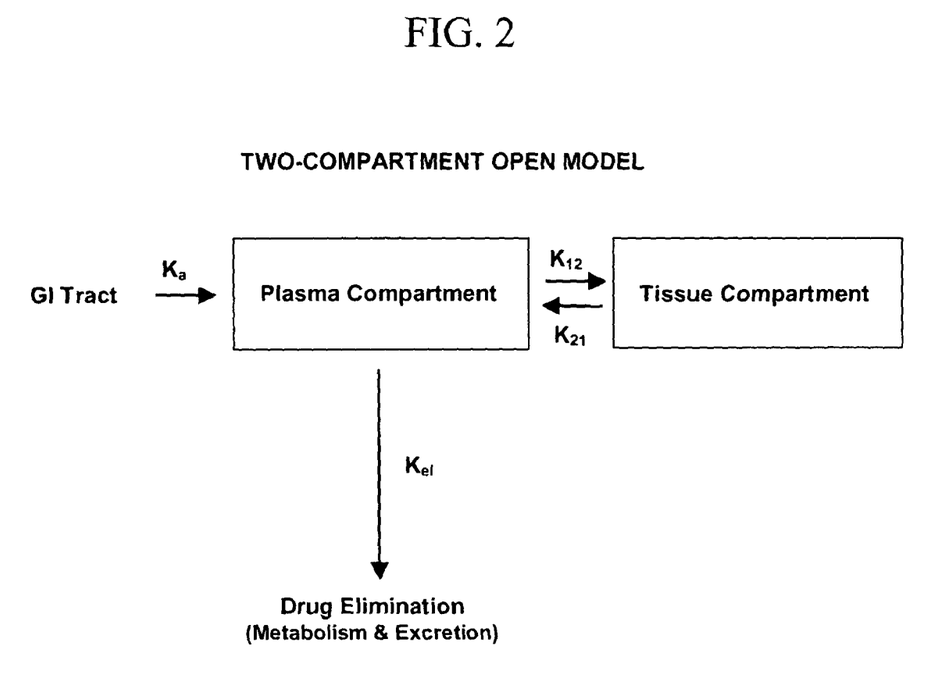
FIG. 2 is a diagram depicting a pharmacokinetic model for the absorption, distribution, and excretion of rifalazil.

The plasma concentration curves are fit to a two-compartment model (see FIG. 2), which is best represented by equation 1. Equations 1-12 can be used to simulate the plasma and tissue concentrations of various dosing regimens based upon the experimentally derived pharmacokinetic parameters. Equation 5 is then used to calculate the amount of rifalazil in the plasma compartment. Low-dosage regimens are simulated using constants derived from PK parameters for 2.5 mg oral dose in male subjects (see Table 1 below).

$$y = A_1 e^{-\alpha t} + B_1 e^{-\beta t} + C_1 e^{-k_a t}; \text{ where} \quad \text{Equation 1}$$

$$AUC_\infty = (AUC_{Tlast} + Cp/\beta); \quad \text{Equation 2}$$

$$Clearance/F = Dose/AUC_\infty; \text{ and} \quad \text{Equation 3}$$

$$\text{Volume of distribution} = V_d\beta/F = Cl/\beta; \quad \text{Equation 4}$$

Plasma concentrations at any given dose may be simulated by $$C_p = k_a FD/V_c[(k_{21} - \alpha)/\{(k_a - \alpha)(\beta - \alpha)\}]e^{-\alpha t} + \quad \text{Equation 5}$$
$$\{(k_{21} - \beta)/(k_a - \beta)(\alpha - \beta)\}e^{-\beta t} +$$
$$\{(k_{21} - k_a)/(\alpha - k_a)(\beta - k_a)\}e^{-k_a t};$$

Where $$A_1 = k_a FD/V_c[(k_{21} - \alpha)/\{(k_a - \alpha)(\beta - \alpha)\}]; \quad \text{Equation 6}$$

$$B_1 = k_a FD/V_c[(k_{21} - \beta)/\{(k_a - b)(\alpha - \beta)\}]; \quad \text{Equation 7}$$

$$C_1 = k_a FD/V_c[(k_{21} - k_a)/\{(\alpha - k_a)(\beta - k_a)\}]; \quad \text{Equation 8}$$

$$Vc/F = k_a Dose/A_1(k_a - \alpha) + A_2(k_a - \beta); \quad \text{Equation 9}$$

$$k_{e1} = \alpha\beta/k_{21}; \text{ and} \quad \text{Equation 10}$$

$$k_{12} + \alpha + \beta - k_{21} - k_{e1}; \text{ and} \quad \text{Equation 11}$$

The amount of drug in the Tissue Compartment may be simulated by:

$$A_T = k_{12} k_a FD[\{e^{-\alpha t}/(k_a - \alpha)(\beta - \alpha)\} + \quad \text{Equation 12}$$
$$\{e^{-\beta t}/(k_a - \alpha)(\alpha - \beta)\} +$$
$$\{e^{-k_a t}/(\alpha - k_a)(\beta - k_a)\}].$$

In equations 1-12 above, $\alpha$ is a "hybrid" distribution rate constant to and from the tissue compartment; $\beta$ is a "hybrid" elimination rate constant by all processes describing terminal elimination; $k_a$ is the absorption rate constant; Cp is the plasma concentration; Vd$\beta$ is the volume of distribution; F is the fraction of administered dose absorbed; and $A_T$ is the amount of rifalazil in the tissue compartment.

TABLE 1

Dose-normalized pharmacokinetic parameters for males following oral administration of single 2.5 mg and 50 mg doses of rifalazil.

| Parameters | Dosing Level | |
|---|---|---|
| | 2.5 mg | 50 mg |
| $C_{max}$ (ng/mL) | 7.9 | 57.3 |
| AUC (ng/mL × hr) | 185.2 | 1347 |
| Absorption t½ (hr) | 0.67 | 0.50 |
| $K_{10}$ (hr$^{-1}$) | 0.045 | 0.039 |
| $K_{12}$ (hr$^{-1}$) | 0.044 | 0.018 |
| $K_{21}$ (hr$^{-1}$) | 0.011 | 0.009 |
| Distribution t½ (hr) | 7.3 | 11.6 |
| Elimination t½ (hr) | 139.2 | 116.2 |
| $V_1/F$ (L/kg) | 4.08 | 12.7 |
| $V_d\beta/F$ (L/kg) | 36.0 | 82.4 |
| (Cl/F)/kg (L/hr/kg) | 0.18 | 0.49 |

Example 2

Simulations

Using the pharmacokinetic (PK) parameters derived for 2.5 mg oral dosing in male subjects and equations 1-12 above, the simulated plasma and tissue rifalazil concentrations were calculated for a single 2.5 mg oral; a single 1.0 mg oral; a single 0.25 mg oral; five daily 1.0 mg oral; and five daily 0.25 mg oral rifalazil administrations (Table 1). The simulations are based on the pharmacokinetic parameters derived from the plasma concentration data following administration of a single 2.5 mg dose of rifalazil and is based on an assumed bioavailability of 25% (the actual bioavailability in man is currently unknown but this value is consistent with animal data).

Figure 3:
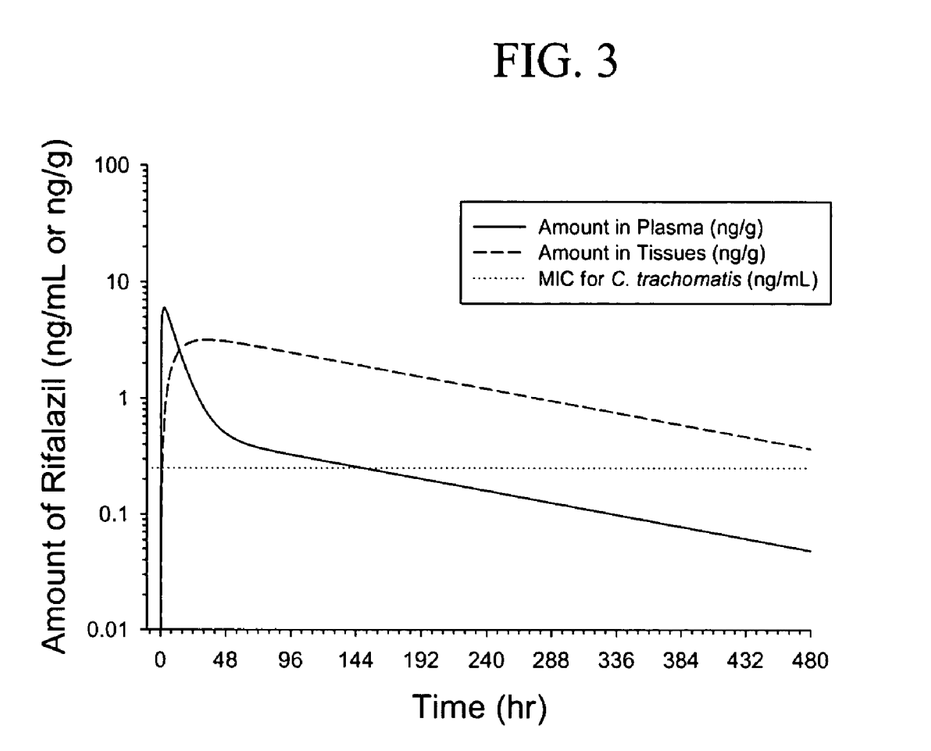
FIG. 3 is a log-graph depicting the simulated rifalazil concentrations in plasma and tissue following a single 2.5 mg oral administration of rifalazil relative to the MIC for *C. trachomatis*.

At 2.5 mg single dose, the simulated PK curve shows that the tissue concentration of rifalazil remains above the MIC for *C. trachomatis* for greater than 500 hours (FIG. 3).

Figure 4:
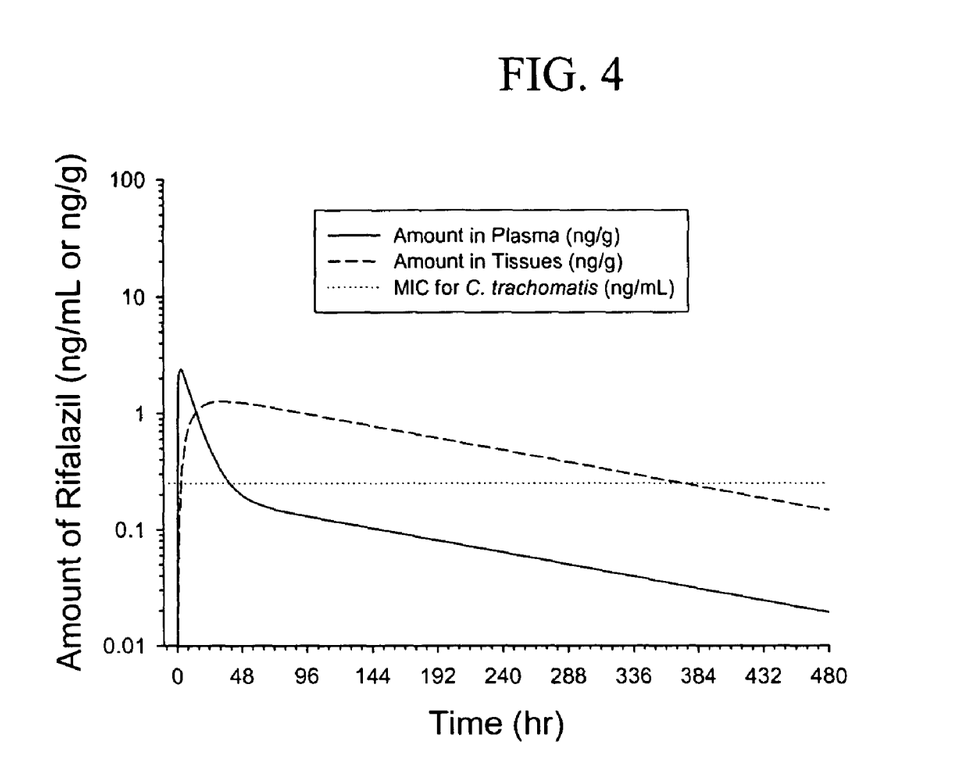
FIG. 4 is a log-graph depicting the simulated rifalazil concentrations in plasma and tissue following a single 1.0 mg oral administration of rifalazil relative to the MIC for *C. trachomatis*.

At 1.0 mg single dose, the simulated PK curve shows that the plasma and tissue concentrations of rifalazil remains above the MIC for *C. trachomatis* for greater than 48 and 350 hours, respectively (FIG. 4).

Figure 5:
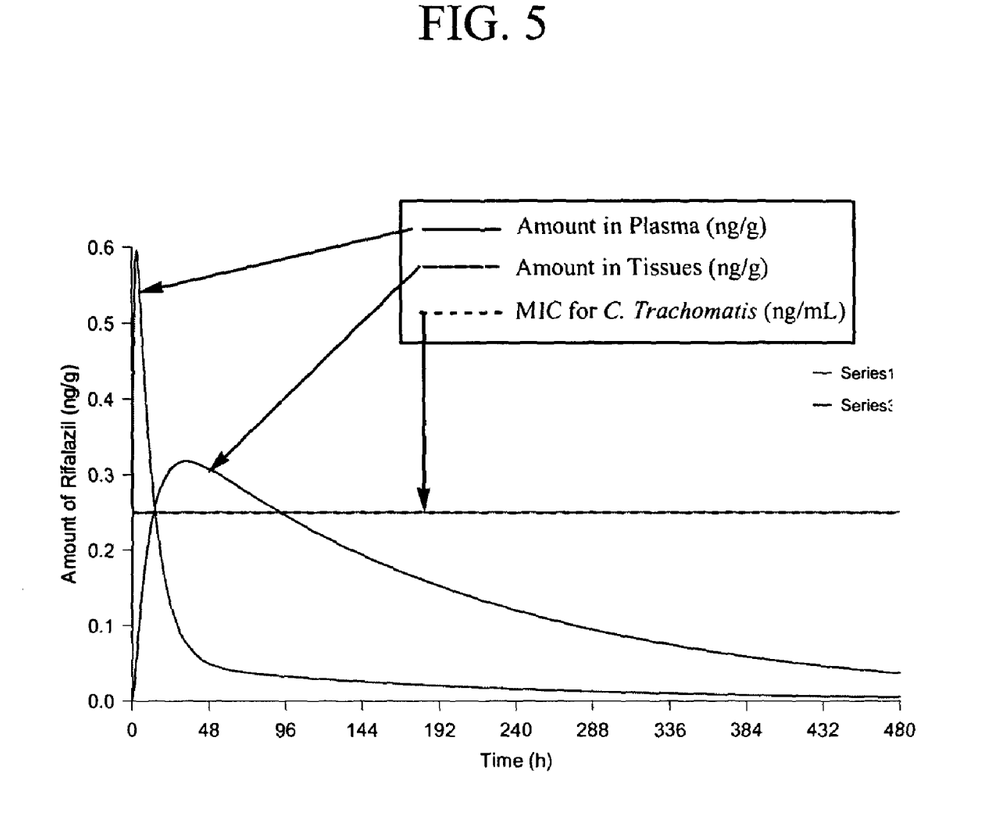
FIG. 5 is a graph depicting the simulated rifalazil concentrations in plasma and tissue following a single 0.25 mg oral administration of rifalazil relative to the MIC for *C. trachomatis*.

At 0.25 mg single dose, the simulated PK curve shows that the plasma and tissue concentrations of rifalazil remains above the MIC for *C. trachomatis* for greater than 24 and 96 hours, respectively (FIG. 5).

Figure 6:
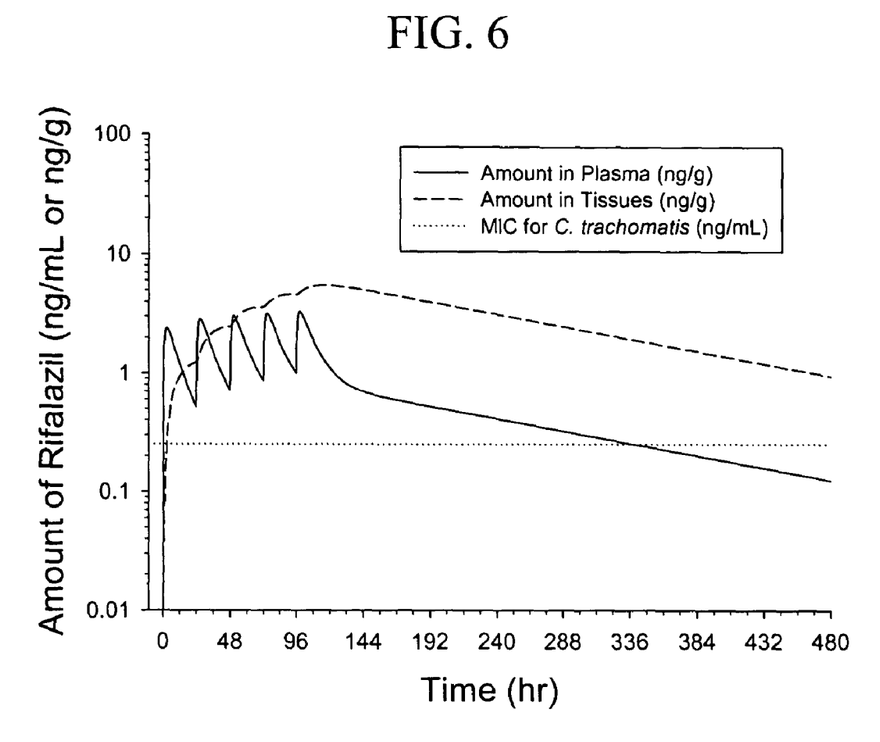
FIG. 6 is a log-graph depicting the simulated rifalazil concentrations in plasma and tissue following five daily 1.0 mg oral administrations of rifalazil relative to the MIC for *C. trachomatis*.

With a multiple dose regimen of 1.0 mg daily for 5 days, the simulated PK curve shows that plasma and tissue concentrations of rifalazil remain above the MIC for *C. trachomatis* for greater than 336 hours and 3 weeks, respectively (FIG. 6).

Figure 7:
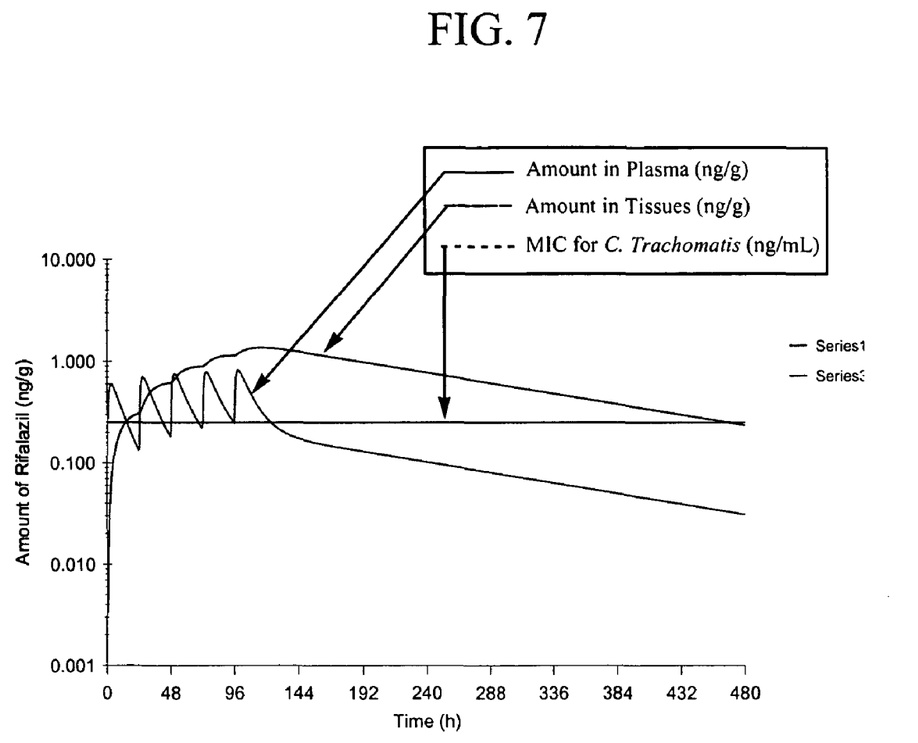
FIG. 7 is a log-graph depicting the simulated rifalazil concentrations in plasma and tissue following five daily 0.25 mg oral administrations of rifalazil relative to the MIC for *C. trachomatis*.

With a multiple dose regimen of 0.25 mg daily for 5 days, the simulated PK curve shows that plasma and tissue concentrations of rifalazil remain above the MIC for *C. trachomatis* for 24 hours and 480 hours, respectively (FIG. 7).

Other Embodiments

All publications, patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A pharmaceutical composition comprising a unit dosage form of rifalazil in an amount of 0.25 mg.

2. A pharmaceutical composition according to claim 1, wherein said unit dosage is a tablet, pill, capsule, or caplet.

3. A pharmaceutical composition comprising a unit dosage form of rifalazil in an amount between 0.2 and 0.7 mg.

4. The pharmaceutical composition of claim 3, wherein said unit dosage is a tablet, pill, capsule, or caplet.

* * * * *